(12) United States Patent
Siegler et al.

(10) Patent No.: US 8,500,668 B2
(45) Date of Patent: Aug. 6, 2013

(54) ORTHOSIS AND METHOD OF USE FOR TREATMENT AND REHABILITATION OF DROPFOOT

(75) Inventors: Sorin Siegler, Merion, PA (US); Brett W. Hraban, Omaha, NE (US); Elizabeth La Montagne, Philadelphia, PA (US); Joshua Meles, Philadelphia, PA (US); Wei Sun, Cherry Hill, NJ (US)

(73) Assignee: Drexel University, Philadelphia, PA (US)

( * ) Notice: Subject to any disclaimer, the term of this patent is extended or adjusted under 35 U.S.C. 154(b) by 555 days.

(21) Appl. No.: 12/305,878

(22) PCT Filed: Jun. 29, 2007

(86) PCT No.: PCT/US2007/072535
§ 371 (c)(1),
(2), (4) Date: Jun. 22, 2010

(87) PCT Pub. No.: WO2008/005865
PCT Pub. Date: Jan. 10, 2008

(65) Prior Publication Data
US 2010/0262044 A1 Oct. 14, 2010

Related U.S. Application Data

(60) Provisional application No. 60/806,364, filed on Jun. 30, 2006.

(51) Int. Cl.
*A61F 5/00* (2006.01)
*A61F 5/37* (2006.01)
*A61F 2/68* (2006.01)

(52) U.S. Cl.
USPC ............... 602/23; 602/28; 128/882; 623/53

(58) Field of Classification Search
USPC .............. 602/23, 16, 5, 27, 28; 128/882, 869, 128/846, 845, 905; 601/5; 623/53
See application file for complete search history.

(56) References Cited

U.S. PATENT DOCUMENTS

| 5,112,296 | A | 5/1992 | Beard et al. |
| 5,121,747 | A | 6/1992 | Andrews |

(Continued)

OTHER PUBLICATIONS

Kern, H., et al.; Denervated muscles in humans: limitations and problems of currently used functional electrical stimulation training protocols; Artificial Organs; Apr. 4, 2002; 26(3); 216-218.

(Continued)

*Primary Examiner* — Victoria J Hicks
(74) *Attorney, Agent, or Firm* — Mendelsohn, Drucker & Associates, P.C.

(57) ABSTRACT

A functional electrical stimulation brace responsive to various positions of an intended wearer's foot. The device includes a plurality of sensors positioned at different locations under the intended wearer's foot to detect the current position of the foot. Outputs from the sensors are fed to a controller that uses logic to activate an electrical stimulation unit that stimulates the peroneal muscles of a patient at the appropriate times during the patient's gait. The device may also employ mechanical stabilization of the ankle in addition to the functional electrical stimulation by means of an ankle foot orthosis with a variable resistance hinge. The electrodes are embedded in fixed locations in the brace upper portion so that optimal location of the electrodes relative to the peroneal muscles is maintained every time the device is applied. Also provided is a method for assistance and rehabilitation for a patient by electrical stimulation of the peroneal muscles. In the method, the position of the foot is detected and the peroneal muscles are stimulated responsive to particular positions of the patient's foot in order to activate the muscles at the appropriate times during the patient's gait. The device also provides lateral and torsional stability by means of the ankle-foot orthosis.

14 Claims, 5 Drawing Sheets

U.S. PATENT DOCUMENTS

| | | |
|---|---|---|
| 5,306,230 A | 4/1994 | Bodine |
| 5,476,441 A | 12/1995 | Durfee et al. |
| 5,643,332 A | 7/1997 | Stein |
| 5,748,845 A | 5/1998 | Labun et al. |
| 5,814,093 A | 9/1998 | Stein |
| 6,377,178 B1 | 4/2002 | DeToro et al. |
| 6,507,757 B1 | 1/2003 | Swain et al. |
| 6,602,217 B2 | 8/2003 | Crawford et al. |
| 6,676,618 B2 | 1/2004 | Andersen |
| 6,926,687 B2 | 8/2005 | Shields |
| 2005/0070834 A1 | 3/2005 | Herr et al. |

OTHER PUBLICATIONS

LaMontagne, E., et al.; "Let's Walk" Ankle Foot Orthotic Development; College of Engineering, Drexel University; Mar. 26, 2007; pp. 1-21; Retrieved from Drexel E-Repository and Archive (iDEA) http://idea.library.drexel.edu/.

|  | SWITCH 12A | SWITCH 12B | SWITCH 12C | SWITCH 12D |
| --- | --- | --- | --- | --- |
| FOOT FLAT | CLOSED | CLOSED | CLOSED | CLOSED |
| HEEL OFF | ACTIVATED | ACTIVATED | ACTIVATED | CLOSED |
| SWING THROUGH | ACTIVATED | ACTIVATED | ACTIVATED | ACTIVATED |
| HEEL STRIKE | CLOSED | ACTIVATED | ACTIVATED | ACTIVATED |
| BALL STRIKE | CLOSED | CLOSED | CLOSED | ACTIVATED |
| TOE STRIKE | CLOSED | CLOSED | CLOSED | CLOSED |

*FIG. 5*

ORTHOSIS AND METHOD OF USE FOR TREATMENT AND REHABILITATION OF DROPFOOT

BACKGROUND OF THE INVENTION

1. Field of the Invention

The invention relates to the field of rehabilitation. In particular the invention relates to foot and ankle orthoses and methods for using them.

2. Description of the Related Technology

Drop foot is a common medical condition that has its source in various different pathological conditions. The condition can be caused by trauma in which the peroneal nerve that innervates the peroneal muscles is damaged. Drop foot can also be present following a stroke or it can be congenital.

The traditional treatment for drop foot deformity involves the use of a rigid ankle/foot brace also known as an orthosis. The ankle/foot brace maintains the ankle rigid and in a neutral position. This fixed brace, which does not allow motion at the ankle, suffers from several problems. One of the problems is the interference with normal ankle function due to the fact that this brace maintains the ankle rigid. This increases the risk of soft tissue contracture and other pathologies resulting from long-term, joint immobilization. Another problem is that, since the ankle is fixed by the brace and the peroneal muscles are not stimulated, the muscles degenerate and lose their viability and mass. Furthermore, since the ankle joint is held fixed, the ability to perform activities that require ankle movement is limited.

Functional Electrical Stimulation (FES) is a well-established field of research and its foundation is based on the fact that a muscle can be externally stimulated to contract by a current having a specific shape, strength and frequency through skin-electrodes overlying the muscle or through electrodes implanted beneath the skin. Some attempts have been made to use FES in the treatment of patients with drop foot. However, these attempts were quite limited and impractical for everyday use for several reasons. For example, they did not provide a method to consistently apply the electrodes in their optimal location. The stimulation provided was based on very limited and insufficient information from either the leg inclination or from the heel maintaining contact with the ground. No lateral stability was provided and no microprocessor was used to process the input signals and generate appropriate action through stimulation of the peroneal muscles. Finally, and perhaps most importantly, conventional FES is well known to result in quick fatigue of the stimulated muscles. Once fatigue sets in, the muscles can not perform their function appropriately and dropfoot again becomes a problem. Conventional FES methods do not provide means of overcoming or addressing this critical problem.

Therefore there exists a need for providing an FES brace that can be easily applied and maintained by the patient, without the need for intervention of a physical therapist each time the brace must be used and which provides consistent optimal placement of the FES electrodes against the skin each time the brace is applied. This FES brace should also provide controlled, meaningful stimulation of the peroneal muscles based on information from the foot-ground interaction. Finally, the FES brace should provide a means to lock the joint in a fixed position and cease stimulation in a controlled periodic manner thus avoiding the problem of fatigue.

SUMMARY OF THE INVENTION

Accordingly, it is an object of certain embodiments of the invention to provide an FES brace that can be easily applied and maintained by the patient, without the intervention of a physical therapist, and which can provide controlled, intermittent, meaningful stimulation of the peroneal muscles.

According to a first aspect of the invention, there is provided an FES brace including a plurality of stimulating electrodes, a controller, a solenoid for locking the joint of the brace, a plurality of sensors operably connected to the controller and a device for stimulating the electrodes in response to a signal from the controller. The plurality of sensors is positioned relative to one another to detect various interaction events between the foot of the person and the ground in order to cause stimulation of the electrodes in response to the sensed foot-to-ground interaction. The FES brace includes an ankle-foot orthosis made of an upper part fixed to the shank of the patient and a lower part fixed to the foot of the patient. The two parts are connected together through a joint with a variable resistance such that the joint can be completely locked, completely free to move or is able to move with a controlled amount of resistance.

According to second aspect of the invention, a method of delivering consistent stimulation to the peroneal muscles through electrodes embedded inside the shank portion of the ankle-foot orthosis is provided. The method includes the steps of placing at least two electrodes in fixed locations inside the shank portion of the brace which contact the skin overlying the peroneal muscles of a patient for delivery of stimulation, detecting a plurality of positions of the patient's foot with a plurality of sensors and transmitting activation signals to the electrodes based upon the detected positions of the patients' foot.

According to a third aspect of the present invention, there is provided a brace having an upper portion provided with a plurality of electrodes, a lower portion pivotally connected to the upper portion, a controller, and a plurality of sensors operably connected to the controller. The controller is operably connected to the plurality of electrodes to control the electrodes responsive to a signal from the controller. In addition, adjustable timing circuitry is provided. This circuitry overrides the stimulation circuitry through the sensors and provides intermittent recovery periods without stimulation to prevent onset of fatigue. During such recovery periods, the timing circuitry activates the joint solenoid so the joint in the ankle-foot orthosis becomes locked to provide passive resistance.

These and various other advantages and features of novelty that characterize the invention are pointed out with particularity in the claims annexed hereto and forming a part hereof However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 5 is a table of one embodiment the activated/closed status of the sensors during different walking positions.

DETAILED DESCRIPTION OF THE PREFERRED EMBODIMENT(S)

Drop foot is a problem that interferes with normal ambulation. It is the result of a lack of neural control of the peroneal muscles. The peroneal muscles are responsible for dorsiflexion of the foot (bringing the toes up or preventing the toes from slamming against the floor). Instead of the rigid ankle/foot brace typically used to treat drop foot, the present invention provides an improved Functional Electrical Stimulation (FES) brace that enables improved normal ambulatory function by using the patient's own muscles while maintaining good ankle/foot stability through the use of an ankle foot orthosis.

The FES device stimulates the muscles and causes the muscles to contract. As a result, the muscles are maintained in good condition by the FES device. Furthermore, the FES device can be used as part of a rehabilitation program for treatment of drop foot. Such a rehabilitation program would not require special sessions, but instead could form part of the regular activity of the patient, such as taking a walk or exercising on a treadmill.

The FES brace includes an ankle-foot orthosis made of an upper part fixed to the shank of the patient and a lower part fixed to the foot of the patient. The two parts are connected together through a joint with a variable resistance such that the joint can be completely locked, completely free to move or is able to move with a controlled amount of resistance. The ankle-foot orthosis is designed to allow the patient to control the degree of reliance on the FES device. For example, during the initial phase as the patient learns how to use the FES device the patient may set the joint to high resistance. As the patient becomes more comfortable with the brace the resistance can be decreased. Also, if the patient feels fatigued or simply does not want to use the FES, but still use the ankle-foot orthosis, the patient can do so by turning off the stimulation and locking the joint. In addition, adjustable intermittent FES stimulation designed to prevent onset of fatigue is provided. The patient can adjust the duty cycle time, and the FES stimulation will be provided in a periodic fashion. During the periods of non-stimulation, the joint solenoid is activated to maintain the ankle fully stabilized by providing passive resistance to motion of the joint. The upper and lower part of the brace can be made of hard or soft polymeric material.

Figure 1:
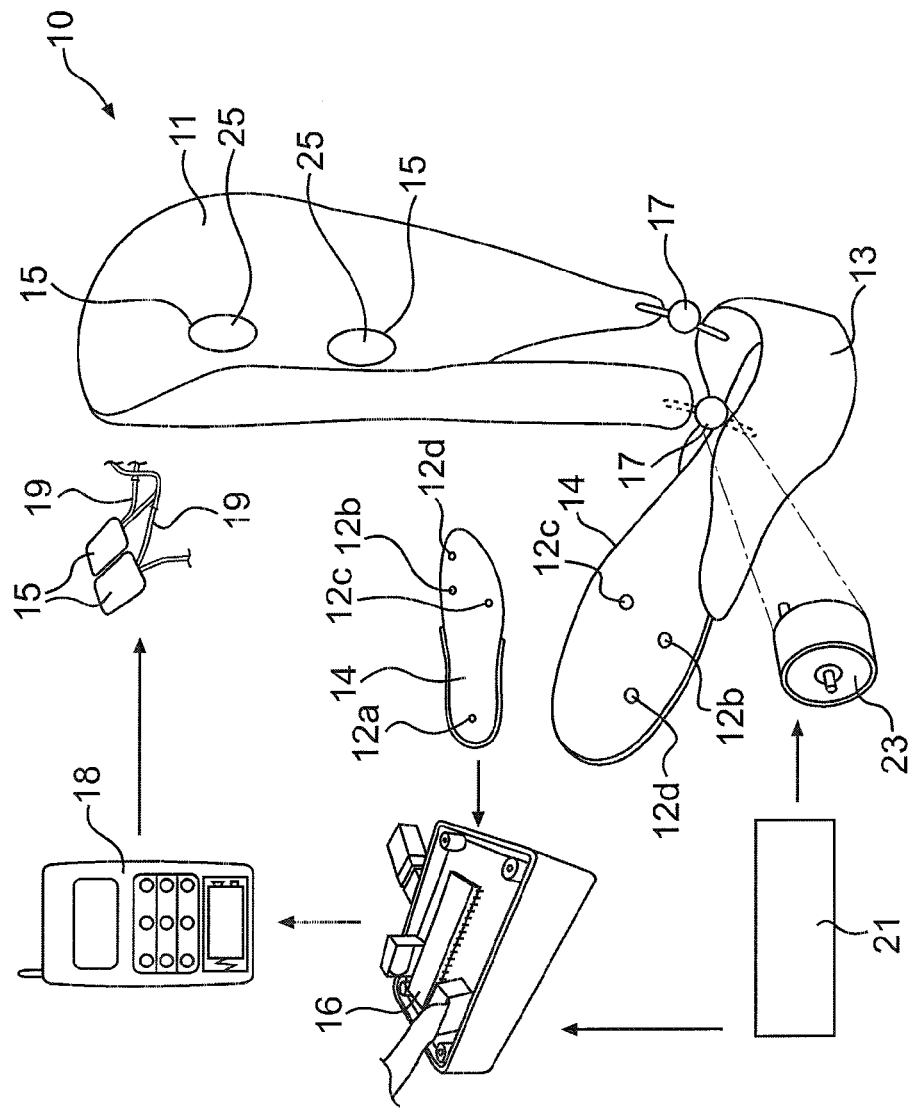
FIG. 1 shows a diagram of one embodiment of an FES device in accordance with the invention.

FIG. 1 shows a diagram of one embodiment of an FES device 10. FES device 10, as shown in FIG. 1, includes an upper portion 11, a lower portion 13 and an insert 14. Upper portion 11 and lower portion 13 can be made of any suitable material. In one embodiment, upper and lower portions 11, 13 are made from a shapeable material such as a thermoplastic material, to thereby permit customization of the upper and lower portions 11, 13 to the contour of a specific patient's leg and foot, by, for example, use of molds of the patient's leg to fabricate upper and lower portions 11, 13. Lower portion 13 preferably fits over the patient's heel and midfoot.

Figure 2:
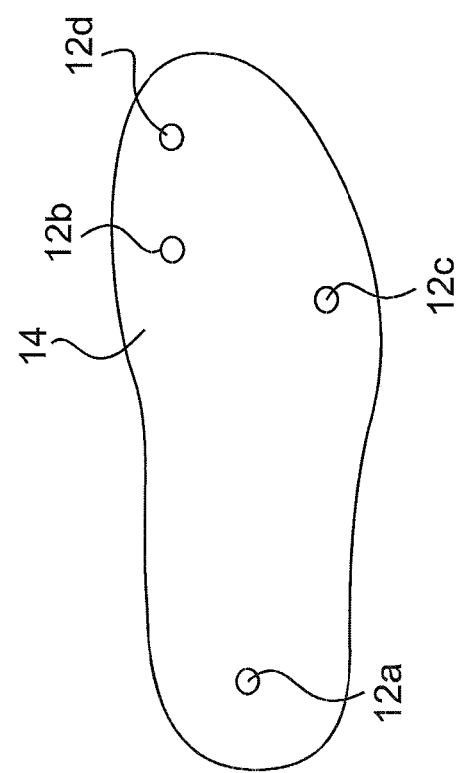
FIG. 2 shows the underside of an insert and one embodiment of a location of the sensors.

FES device 10 comprises an array of sensors 12a-12d, which may be any conventional sensors or switches suitable for use in detecting various positions of a patient's foot. Sensors 12a-12d are shown embedded in thin in-shoe insert 14, which may optionally be made of midsole material, in the embodiment of FIGS. 1-2. Sensors 12a-12d may be located under strategic anatomical locations of the foot of the intended wearer's foot in order to enhance the performance of FES device 10. In the embodiment of FIGS. 1-2, sensor 12a is located under the heel of the intended wearer's foot, sensor 12b is located under the first metatarsal of the intended wearer's foot, sensor 12c is located under the fifth metatarsal of the intended wearer's foot and switch 12d is located under the big toe of the intended wearer's foot. The sensors may be set for activation/deactivation by a pressure of approximately ¼ lb. per square inch.

Alternatively, it is possible to use one or more accelerometers to sense various foot positions of an intended wearer's foot. Suitable, conventional accelerometers may be employed for this purpose. It is also possible to use pressure sensors in order to determine when a certain amount of pressure is placed on a foot by a patient, or other suitable sensors or switches. FES device 10 also includes a controller such as a microprocessor 16 to receive signals from sensors 12a-12d. Microprocessor 16 processes the signals according to their closed-activated pattern and produces an output signal that is sent to an FES unit 18. FES unit 18 may be, for example, a commercial, battery operated, two-channel unit, which accepts remote switch input for its activation/deactivation. The output from microprocessor 16 is fed to the remote switch input of FES unit 18 and FES unit 18 is activated/deactivated responsive to the output from microprocessor 16.

A suitable, portable, two-channel FES unit 18 includes an electronic unit, electrode wires 19 and electrodes 15. The FES unit 18 is provided with the same number of channels as there are electrodes 15. Electrodes 15 may be suitably positioned on upper portion 11 of FES device 10 over the peroneal muscles. Upper portion 11 may include an indication of where electrodes 15 should be attached, or electrodes 15 may be embedded in upper portion 11, thereby only requiring attachment of FES unit 18 to electrodes 15. Alternatively, upper portion 11 may include a mounting structure for mounting electrodes 15 in the proper position on upper portion 11 of FES device 10 or upper portion 11 may be provided with depressions 25 suitably positioned for optimum location of electrodes 15 so that electrodes 15 can be inserted into depressions 25. By positioning electrodes 15 at certain locations, ideal stimulation can be applied to the peroneal muscles without requiring a trained technician to position the FES device each time the brace is used. In one embodiment, at least two electrodes are employed to provide improved stimulation of the peroneal muscles of a single foot. Preferably, the electrodes 15 are located or embedded in fixed locations in the upper portion 11 so that optimal location of the electrodes 15 relative to the peroneal muscles is maintained when the device is in use. The electrodes 15 are preferably designed to fit over the anterior tibialis muscle in a manner which provides optimal stimulation of this muscle group.

FES device 10 may include a hinge 17 at the level of the ankle joint. Hinge 17 connects lower portion 13 to upper portion 11 to allow lower portion 13 to pivot about hinge 17 relative to upper portion 13, thus permitting dorsiflexion/plantarflexion motion while providing good lateral stability. The hinge 17 is provided with a device, such as a solenoid 23, which allows the patient to set the desired amount of resistance that the hinge 17 will provide. For example, hinge 17 can be completely locked to make the brace completely rigid, in which case no muscle contraction is required to maintain a stable ankle and the muscles are allowed to recover in order to prevent the onset of fatigue. Hinge 17 can also be completely open so as to provide zero resistance. Any setting in between locking hinge 17 and hinge 17 providing zero resistance may also be selected by the patient to provide partial assistance to the muscles. As discussed above, the variable resistance provided by hinge 17 can be used by the patient as part of the rehabilitation process, for example, to increase the effort required for walking to provide additional exercise for the muscles, for comfort or to adjust the patient's particular needs at different points in the rehabilitation process.

The purpose of sensors 12a-12d is to detect the state of interaction between the foot and the ground. Based on this interaction, a decision is made by microprocessor 16 whether to stimulate the peroneal muscles or not. Switches 12a-12d are embedded in thin shoe insert 14 in this embodiment. The insert 14 may be positioned inside the intended wearer's shoe. Wires from switches 12a-12d are connected as inputs to microprocessor 16.

Adjustable timing circuitry 21, to provide intermittent FES stimulation while at the same time providing intermittent resistance at the joint, may also be included. A clock included with the adjustable timing circuitry 21 provides periodic on/off signals. The length of the on/off period can be adjusted by the patient or by a clinician. During the "on" period, the timing circuitry 21 provides two functions. It disables the FES stimulation 18 to stop stimulation of the muscles and it provides a signal to the solenoid 23 which, in turn, provides passive resistance at the joint, creating a rigid, stable brace. During the "off" period, the timing circuitry 21 is disabled thus allowing normal function of the FES stimulation unit 18 and the joint solenoid 23. This intermittent control of FES stimulation and, joint resistance acts to prevent the onset of fatigue during functional activities such as walking, while at the same time maintaining a stable joint that functions well.

The operation of the timing circuitry 21 is as follows. The patient when starting an activity, for example walking, activates the timing circuitry 21. During the activity, the timing circuitry 21 periodically activates and de-activates the solenoids 23. During the periods that the solenoids 23 are activated, the timing circuitry 23 interrupts excitation from the FES unit 18. This process is repeated throughout the duration of the activity until the timing circuitry 21 is deactivated by the patient.

For bi-lateral drop foot conditions, two FES devices 10 may be used, with one such device 10 being positioned on each foot. It is possible to use more or fewer sensors depending on the desired level of complexity of the device. Having more sensors may assist in compensating for various walking styles including more unusual walking styles. The addition of more sensors may also improve the timing of stimulation by FES unit 18. Having more sensors provides additional information that can be employed to generate signals to FES unit 18. This permits more precise operation of the FES device 10. It also provides a backup mechanism, in the case that one or more sensors may not be operational since the remaining operational sensors can still trigger stimulation even if one or more sensors should fail.

Having fewer sensors reduces the overall cost and complexity of the device. In one embodiment, FES unit 18 could be activated by a single sensor that is closed when the intended wearer is standing still and which is activated when the location of the sensor under the intended wearer's foot leaves the ground. However, the tradeoff would be less precise control of FES unit 18 since stimulation would only occur when a specific part of the foot left the ground, whereas in the FES device 10 with four sensors, stimulation may be programmed to occur under various sensor combinations. As a result, it is desirable to employ at least two, and preferably, at least four sensors in the FES device 10 of the present invention. In the depicted embodiment, microprocessor 16 receives four input signals from sensors 12a-12d. It processes these input signals and, based on the sensor pattern, microprocessor 16 generates an output signal which activates or de-activates FES unit 18. Microprocessor 16 is programmed to deal with a wide array of ambulatory demands such as walking at various speeds, walking up and down inclines, walking up and down stairs, initiating a walk and coming to a stop from a walk, sitting down and standing up and turning. Handling such wide array of conditions requires multiple sensors as described in this embodiment, rather than using only one sensor.

Figure 3A:
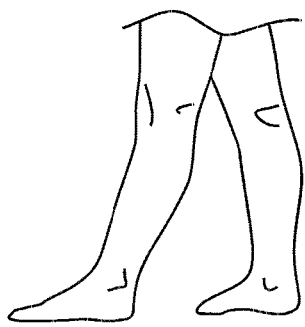
FIG. 3a shows the foot flat position during the walking cycle.
Figure 3B:
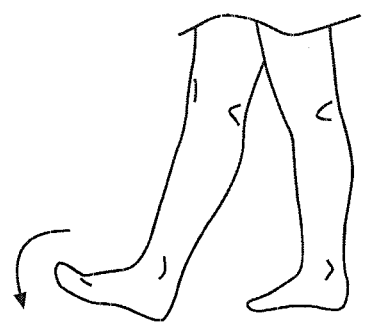
FIG. 3b shows the heel strike position during the walking cycle.
Figure 3C:
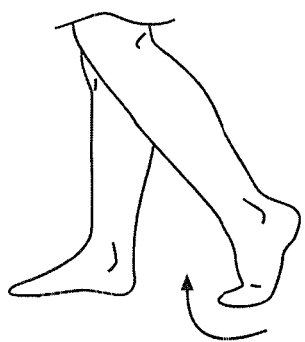
FIG. 3c shows the toe off position during the walking cycle.
Figure 3D:
FIG. 3d shows the heel off position during the walking cycle.
Figure 3E:
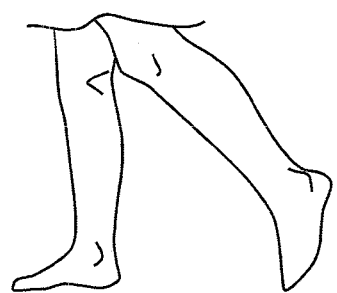
FIG. 3e shows the swing through position during the walking cycle.

One simple example that demonstrates the logic of activation/de-activation is provided in the figures for the common activity of walking on a level surface. FIGS. 3a-3e show the events that occur during the walking cycle on level ground. FIG. 3a shows the foot flat position when the peroneal muscles are inactive. FIG. 3b shows the heel strike position where the peroneal muscles are active in order to decelerate forward foot rotation. FIG. 3c shows the toe off position where the peroneal muscles are active to bring the toes up for clearing the ground during the swing of the foot. FIG. 3d is the heel off position where the peroneal muscles are inactive. FIG. 3e is the swing through position where the peroneal muscles are active in order to keep the toes up and to prevent the toes from striking the ground.

Figure 4A:
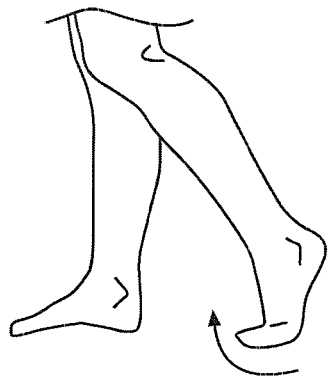
FIG. 4a shows the toe off position during the walking cycle of a patient with drop foot.
Figure 4B:
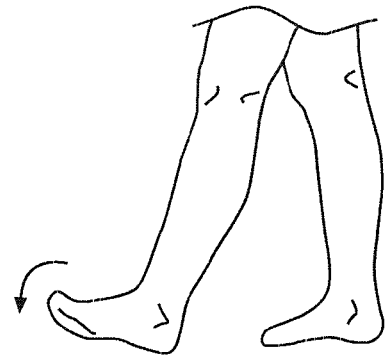
FIG. 4b shows the heel strike position during the walking cycle of a patient with drop foot.
Figure 4C:
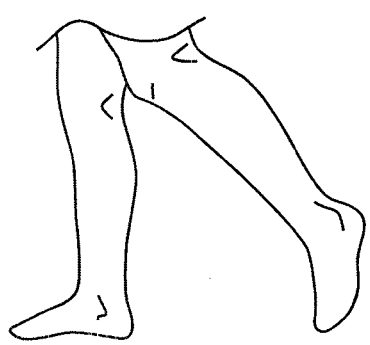
FIG. 4c shows the swing through position during the walking cycle of a patient with drop foot.

FIGS. 4a-4c show the events during the walking cycle affected by the inability of the peroneal muscles to contract, i.e. drop foot condition. FIG. 4a shows the affected toe off position where the toes cannot clear the ground unless the patient elevates the hip to compensate. FIG. 4b shows the affected heel strike position where the forefoot slaps against the ground. FIG. 4c shows the affected swing through position where the toes drop towards the ground thereby preventing efficient clearing and requiring increased elevation of the hip to compensate. Based on FIGS. 3a-3e and 4a-4c, suitable logic for peroneal muscle activation using as sensors, foot switches 12a-12d, is demonstrated below. The moment the involved foot contacts the ground is referred to as "heel strike" and is shown in FIGS. 3b and 4b. During this position heel switch 12a is closed and all others are open. Microprocessor 16 sends an "activate" signal to FES unit 18. As a result, the peroneal muscles are contracted to decelerate the foot as it quickly rotates forward, thus preventing slapping of the foot against the ground. Immediately after heel strike, the foot is quickly rotated forward until the toes come into contact with the ground and switches 12b-12c are closed in addition to switch 12a. Since during this phase no peroneal muscle activation is required microprocessor 16 sends a signal to FES unit 18 to de-activate.

As the stance phase progresses and the heel starts to rise from the ground into the "heel off" position, the heel switch 12a opens followed by switches 12b and 12c. Once all of switches 12a-12c are open, microprocessor 16 sends an activation signal to FES unit 18 so that the peroneal muscles again contract and cause dorsiflexion of the foot to clear the ground during the swing phase. Activation continues until the next "heel strike" and the pattern repeats itself. The example above demonstrates the role played by microprocessor 16 in generating properly timed activation signals to FES unit 18.

FIG. 5 is a table further illustrating the various positions during the walking cycle that activate switches 12a-12d. As can be seen from the table, during the foot flat position, shown in FIG. 3a, switches 12a-12d are closed. In the heel off position, shown in FIG. 3d switches 12a-12c are activated, thereby instructing FES unit 18 to stimulate the peroneal muscles. In the swing through position, shown in FIGS. 3e and 4c, all of switches 12a-12d are activated. In the heel strike position, shown in FIGS. 3b and 4b, switch 12a is closed, while switches 12b-12c are activated, thereby causing FES unit 18 to stimulate the peroneal muscles. In the ball strike position, not shown, all switches 12a-12c are closed, while switch 12d remains activated. In the toe strike position, not shown, switches 12b-12d are closed. The use of the four switches enables improved timing of the activation of the FES unit 18, relative to a device that only employs a single switch.

Different numbers of sensors and different logic may be employed to offer more precise control, to save costs, or, for example, to compensate for an unusual gait. In the latter case, additional sensors can be positioned at other locations of the foot to provide timely activation of the electrodes in response to the particular foot strike pattern of a particular user than may have an unusual gait.

The FES device of the present invention can be implemented in a variety of different ways. The controller and FES unit can be operably connected to the sensors and electrodes via wires, wirelessly or by a combination of wires and wireless connections. The sensors, electrodes, controller and FES unit may be separated into a separate device from the brace or one or more of the sensors, electrodes, controller and FES unit may be attached to, or integrated into the brace. For example, the insert containing the sensors can be attached to the lower portion 11 of the brace, if desired, or the insert can be a separate piece.

In an advantageous embodiment, the brace and FES device are completely integrated as shown, for example, in FIGS. 1-2. In variations of this embodiment, the controller and FES unit may be affixed to or integrated into the brace for ease of use.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An ankle-foot orthosis comprising:
an upper portion,
a lower portion pivotally connected to the upper portion by a hinge capable of providing variable resistance to movement of said upper portion relative to said lower portion,
at least one sensor;
a controller operably connected to receive input from each said at least one sensor and generate an output based on said input,
an electrical stimulation unit operably connected to said controller,
at least one electrode associated with at least one of said upper and lower portions of said orthosis for stimulation of at least one peroneal muscle of an intended wearer when said orthosis is worn by said intended wearer, said at least one electrode being operably connected to said electrical stimulation unit for activation by said electrical stimulation unit responsive to the output from said controller, and
adjustable timing circuitry which intermittently prevents operation of the electrical stimulation unit while simultaneously causing the hinge to increase the variable resistance to movement of the upper portion of the ankle-foot orthosis relative to the lower portion of the ankle-foot orthosis.

2. The orthosis of claim 1, wherein said orthosis comprises at least four said sensors.

3. The orthosis of claim 2, wherein said at least four said sensors are associated with the lower portion of said orthosis such that said at least four said sensors are located at specific locations beneath the intended wearer's foot when said orthosis is worn by the intended wearer.

4. The orthosis of claim 3, wherein one of said at least four sensors is positioned for location under a heel of the intended wearer's foot and a second of said at least four said sensors is positioned for location under a toe of said intended wearer's foot.

5. The orthosis of claim 4, wherein said second of said at least four said sensors is positioned for location beneath a big toe of said intended wearer's foot.

6. The orthosis of claim 5, wherein a third of said at least four said sensors is positioned for location beneath a first metatarsal of said intended wearer's foot.

7. The orthosis of claim 6, wherein a fourth of said at least four said sensors is positioned for location beneath a fifth metatarsal of said intended wearer's foot.

8. The orthosis of claim 1, wherein said upper portion is adapted to cover at least a portion of the intended wearer's leg at the location of the at least one peroneal muscle, and said lower portion being adapted to provide stability to an ankle of the intended wearer's foot, such that a combination of said upper and lower portions provides lateral stability to the intended wearer's ankle.

9. The orthosis of claim 8, further comprising a solenoid operatively connected to the adjustable timing circuitry, said solenoid causing the hinge to lock to prevent relative movement between said upper and lower portions when said adjustable timing circuitry prevents operation of said electrical stimulation unit.

10. The orthosis of claim 9, wherein said hinge can be set to provide no resistance to relative motion between said upper and lower portions.

11. The orthosis of claim 10, wherein said at least one electrode is positioned on said upper portion.

12. The orthosis of claim 1, wherein said controller comprises a microprocessor.

13. The orthosis of claim 1, wherein said orthosis comprises at least two said sensors.

14. The orthosis of claim 1, wherein said orthosis comprises at least three said sensors.

* * * * *

UNITED STATES PATENT AND TRADEMARK OFFICE
CERTIFICATE OF CORRECTION

PATENT NO. : 8,500,668 B2  
APPLICATION NO. : 12/305878  
DATED : August 6, 2013  
INVENTOR(S) : Siegler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1229 days.

Signed and Sealed this

Fifteenth Day of September, 2015

Michelle K. Lee
*Director of the United States Patent and Trademark Office*